(12) United States Patent
Ory et al.

(10) Patent No.: US 6,451,032 B1
(45) Date of Patent: Sep. 17, 2002

(54) COMPOSITE PROSTHESIS FOR PREVENTING POST-SURGICAL ADHESIONS AND METHOD FOR OBTAINING SAME

(75) Inventors: François Régis Ory, Fontaines Saint Martin; Michel Therin, Lyons; Philippe Gravagna, Irigny; Jean-Louis Tayot, La Tour de Salvagny, all of (FR)

(73) Assignees: Sofradim Production, Trevoux (FR); Imedex Biomateriaux, Chaponost (FR)

( * ) Notice: Subject to any disclaimer, the term of this patent is extended or adjusted under 35 U.S.C. 154(b) by 0 days.

(21) Appl. No.: 09/463,313

(22) PCT Filed: Jul. 22, 1998

(86) PCT No.: PCT/FR98/01626

§ 371 (c)(1),
(2), (4) Date: Jan. 24, 2000

(87) PCT Pub. No.: WO99/06080

PCT Pub. Date: Feb. 11, 1999

(30) Foreign Application Priority Data

Aug. 1, 1997 (FR) .............................................. 97 10104

(51) Int. Cl.[7] .............................................. A61B 17/04

(52) U.S. Cl. ........................................ 606/151; 424/445

(58) Field of Search ........................... 606/151; 424/445

(56) References Cited

U.S. PATENT DOCUMENTS 4,060,081 A * 11/1977 Yannas et al. .............. 606/151
5,376,376 A * 12/1994 Li ................................ 424/443

FOREIGN PATENT DOCUMENTS

| EP | 0 372 969 A1 | 6/1990 |
| WO | WO 89/08467 | 9/1989 |
| WO | WO 95/18638 | 7/1995 |
| WO | WO 96/08277 | 3/1996 |

* cited by examiner

*Primary Examiner*—Gary Jackson
(74) *Attorney, Agent, or Firm*—Oliff & Berridge, PLC

(57) ABSTRACT

The composite prosthesis comprises a prosthetic fabric having a three-dimensional structure separating two surfaces, one of which is open to post-surgical cell colonization. The composite prosthesis further comprises at least one film of a collagenous material linked to the other surface of the prosthetic fabric. The composite prosthesis may be used to prevent post-surgical adhesion.

52 Claims, 7 Drawing Sheets

COMPOSITE PROSTHESIS FOR PREVENTING POST-SURGICAL ADHESIONS AND METHOD FOR OBTAINING SAME

The present invention concerns a composite prosthesis for preventing postsurgical adhesions, and in particular finds application in the field of visceral or parietal surgery. The invention will be described by way of example in relation to a composite prosthesis intended for use in parietal surgery, in the repair of eventrations or hernias.

Postsurgical adhesions include all non-anatomical fibrous connections accidentally induced by a surgical act during the normal process of cicatrization. They may occur in all surgical disciplines regardless of the operation in question. They are generally all the more severe, the greater the surgical trauma and the more affected the tissues which normally ensure the planes of division (interstitial connective tissue, the synovial membranes, the tendon sheaths, peritoneal and pleural serosa, etc.). Any surgical trauma to tissue is followed by a cascade of physiological events, the main times of which can be simplified as follows:

- time zero (t0): surgical trauma, capillary invasion;
- time zero plus a few minutes: coagulation, formation of fibrin network, release of chemotactic factors;
- time zero (t0) plus 12 to 48 hours: influx of leukocytes, predominantly polynuclears;
- time zero (t0) plus 24 hours to 5 days: influx of leukocytes, predominantly macrophages;
- time zero (t0) plus 4 to 8 days: influx of fibroblasts;
- time zero (t0) plus 5 to 14 days: conjunctive differentiation of the cicatricial reaction;
- time zero (t0) plus 15 to 180 days: cicatricial remodeling.

Although some of the exact mechanisms are still unknown, particularly as regards determination of the intensity of the reaction, it appears that the first few days are decisive since they condition the influx of fibroblasts responsible for the formation of adhesions.

For this reason, such postsurgical adhesions can provoke syndromes which can be classed principally as chronic pain, occlusive syndromes and female infertility. Furthermore, they increase very substantially the risks of making errors in follow-up surgery (myocardial or intestinal invasion during repeat thoracotomy or laparotomy), while prolonging the operating times, since the preliminary dissection can be very awkward in such cases.

One solution to this problem consists in interposing a physical barrier between the structures which one does not wish to see adhering. However, the desired barrier effect poses the problem of the intrinsic adhesive power of this barrier. The reason is that if the barrier is made of a nonabsorbable material, it can itself be the source of adhesions over the course of time; and if it is absorbable, its absorption must be sufficiently noninflammatory so as not to cause adhesions itself.

Several properties are therefore necessary if a material is to be able to reduce the risk of adhesions, namely, among others:

- the material of which it is made up or composed must be substantially smooth and nonporous on at least one of its surfaces, so as not to offer space for cell recolonization;
- the surface of the material must limit the original cell adhesion.

In order to remedy this problem, hydrophobic and inert artificial polymers have been used, for example expanded PTFE, or absorbable polymer substances, for example those based on hyaluronates, or on modified cellulose, which substances rapidly form a hydrogel by hydration in the body.

Nevertheless, and in particular in visceral and parictal surgery, but also in orthopedic or neurological surgery, the barrier must also have a certain mechanical strength allowing it to fulfill its function as an element of surgical reconstruction. Generally speaking, the known prosthetic fabrics, particularly in the treatment of parietal insufficiencies, for example hernias and eventrations, afford an additional mechanical strength to the surgical reconstruction. Such fabrics are all the more effective and their local tolerance is all the better, the earlier and the more intimate their tissue integration. For this reason, the most effective of the known prosthetic fabrics for these indications are generally highly porous and are designed in such a way as to be integrated in the body as rapidly as possible. The term "porous" is intended to signify the characteristic according to which at least one of the surfaces of the fabric is rough, so as to present alveoli, distributed regularly or irregularly, and promoting all cell colonization. It is for this reason that upon contact with the viscera for example, these fabrics promote adhesion, which limits their use at the so-called preperitoneal or retroperitoneal sites. Now, in a number of cases, and more particularly in the case of multiple recurring eventrations, implantation strictly in the preperitoneal site is difficult, even impossible, on account of the existence of an extensive deficit of serosa.

There is therefore a requirement to make available a product which is able to solve the problem of preventing postsurgical adhesions, while at the same time offering a prosthetic reinforcement subject to cell recolonization and tissue integration, and which can be used, for example, to treat an eventration involving substantial peritoneal loss, or small eventrations, by laparoscopy, and hernias.

To this end, patent application WO-A-96/08277 describes a composite prosthesis comprising a prosthetic fabric, in this case an absorbable or nonabsorbable lattice, and at least one film of a crosslinked collagenous material, in this case a collagen gel coagulated in the dry state, associated with one surface of the prosthetic fabric. The composite prosthesis thus formed finds an application in the treatment of eventrations and hernias and, according to the inventors, prevents postoperative adhesions because the coliagenous membrane constitutes a zone of separation permitting release of any early postoperative adhesions that may develop. It is apparent from experiments carried out on pigs and described in the application that the absorption time of the collagenous membrane remains long.

Since any absorption of material is relatively proinflammatory, the persistence beyond about ten days of an absorbable material can lead to a delay in the disappearance of inflammatory cells at the site. This persistent presence of active inflammatory cells (essentially macrophages) will trigger an activation cascade resulting in the stimulation of fibroblasts, which themselves are responsible for the direct formation of adhesions. While mesothelial cells, which are responsible for the peritoneal covering, are known for their rapid regeneratability (appearance as of the fifth or sixth day), it is therefore not only unnecessary, but also substantially contrary to the principles of adhesion prevention, to keep the material on which the barrier effect relies beyond eight to ten days after surgery.

Thus, the use of the collagenous membrane combined with the synthetic lattice, as described in the aforementioned patent application, may in some cases be responsible for initial adhesions because of its relatively slow absorption and may therefore be unsuitable for solving the problem of preventing postsurgical adhesions, while at the same time offering a prosthetic reinforcement subject to cell recolonization and tissue integration. Moreover, its relatively slow absorption limits effective and early recolonization of the synthetic lattice, the latter being masked by the collagenous membrane at the moment when it has to be integrated, that is to say during the first two weeks.

Consequently, the subject of the invention is a composite prosthesis of the kind defined in document WO-A-96/08277, allowing effective tissue integration while remaining compatible with rapid absorption of the film of collagenous material.

According to the invention, this compromise is achieved by the cooperation of three characteristics, namely:

a) the choice of a particular lattice, in this case a three-dimensional prosthetic fabric, that is to say a fabric having a certain thickness separating its two surfaces; and one surface of the fabric is open to any postsurgical cell colonization;

b) linkage, at least on the surface, or even to a certain depth, of the collagenous film to the other surface of said fabric, and that is to say that surface on the opposite side from the surface open to cell colonization;

c) and the choice of a particular collagenous material, namely a collagen whose helical structure is, at least partially, thermally denatured without hydrolytic degradation.

This cooperation makes it possible for tissue colonization to develop immediately, completely independently of absorption of the collagenous film, which itself is relatively rapid, for example occurring in about ten days, on account of the retained collagenous material, and without compromising in any way the monolithic character of the composite prosthesis.

By virtue of the invention, the tissue integration time and the collagenous-material absorption time become of the same order of magnitude, which means that in most cases, when the fabric has been completely integrated and is mechanically effective, for example on the internal surface of the abdominal wall, the collagenous material is completely absorbed, thereby excluding any subsequent adherability of the composite prosthesis.

By virtue of the invention, the parietal or visceral integration of the prosthesis is not disturbed by the absorption of the collagenous material.

The term "open surface" is intended to signify that said surface includes alveoli having a certain depth according to the thickness of the three-dimensional fabric, these alveoli passing completely or incompletely through the thickness of the fabric, from one surface to the other. In the case of a complete passage of the alveoli, this will be referred to as an openwork prosthetic fabric.

According to the invention, that surface of the collagenous film opposite the prosthetic fabric is preferably substantially smooth and nonporous.

The prosthetic fabric comprises, for example, two opposed porous surfaces, separated from each other by the thickness of said fabric, but connected to each other by linking yarns.

By way of example, the weave of the prosthetic fabric determines, within the thickness of the latter, a multiplicity of transverse channels or alveoli, which are substantially parallel to one another, opening out on either side of said fabric on the two porous surfaces respectively, and of which the internal section is substantially free of any linking yarn.

Preferably, the collagenous material comprises collagen and at least one macromolecular hydrophilic additive chemically unreactive with respect to collagen.

The expression "chemically unreactive with respect to collagen" should be understood to mean a compound which is incapable of reacting with any collagen present and which in particular does not form covalent bonds with the latter during its crosslinking.

Advantageously, the thickness of the film is less than the thickness of the prosthetic fabric, for example between 2% and 10% of the total thickness of the composite prosthesis, and preferably between approximately 30 $\mu$ and 100 $\mu$m, and more preferably still is approximately 50 $\mu$ to 75 $\mu$.

Preferably, the collagenous material comprises collagen modified by oxidative scission and heating above 37° C., crosslinked in the presence of at least one macromolecular hydrophilic additive chemically unreactive with respect to said collagen.

In general, this collagenous material may be obtained by the following process, which comprises the steps consisting in:

preparing a solution of collagen modified by oxidative scission;

treating said solution by heating to a temperature greater than 37° C.;

mixing the resulting collagenous solution with a solution containing at least one macromolecular hydrophilic additive chemically unreactive with respect to collagen;

adjusting the pH of said mixture to a neutral pH.

The collagenous material which results therefrom and which forms part of the composite prosthesis of the invention is biocompatible and nontoxic and is absorbed in vivo in less than two weeks. It does not matter whether the collagen used to form the collagenous solution is of animal or human origin, but it is preferably native collagen, dissolved at acid pH or after treatment by pepsin digestion. In particular, it may be type I bovine collagen or type I or III human collagen, or else mixtures of the latter in any proportions.

The oxidative scission step preferably takes place with the aid of periodic acid or one of its salts, in order to make it self-crosslinkable, and thus the crosslinking can be carried out without the aid of crosslinking agents.

The film is linked at least on the surface to the prosthetic fabric, and preferably over a certain thickness, by capillary absorption of the constituent fibers in the prosthetic fabric.

Even more preferably, the collagenous material is in the form of a film linked by capillary absorption of the constituent fibers of the prosthetic fabric over a depth of less than 750 $\mu$m, measured from the outer surface of the film.

Advantageously, the macromolecular hydrophilic additive has a molecular weight of greater than 3000 daltons and is preferably a hydrophilic polymer having a molecular weight of between 3000 and 20,000 daltons. Such additives are, for example, polyethylene glycol, polysaccharides, such as starch, dextran and cellulose, and modified polysaccharides carrying carboxylic functional groups. Preferably, the macromolecular hydrophilic additive is polyethylene glycol.

The weight concentration of hydrophilic additive is preferably two to ten times less than that of the collagen. The crosslinking of the collagen may be carried out at a temperature of between 4° C. and 30° C., and preferably between 18° C. and 25° C.

Advantageously, the composite prosthesis includes a film consisting of a collagen, as defined above, and of at least one macromolecular hydrophilic additive in a collagen/hydrophilic additive weight ratio from 1/1 to 9/1, preferably from 2/1 to 4/1 and more preferably 3/1.

According to the invention, a composite prosthesis comprises two surfaces which are different in their respective appearances and functions, namely one surface which is porous or open on one side, in order to accommodate and direct the postsurgical cell colonization, and the other surface which is closed, for tissue separation without adhesion.

The film of collagenous material is preferably continuous, smooth and nonporous, entirely covering the prosthetic fabric, and more preferably projects beyond the edges of the latter in such a way as to protect the prosthesis from visceral contacts, the overshoot being from 5 to 10 millimeters for example.

The film is intimately linked to the fabric by surface penetration, and cannot be delaminated, so as not to constitute a plane of separation, while at the same time maintaining the porosity open on the other surface of the prosthetic fabric.

The film is preferably also flexible so as to preserve the handleability of the product, and its possible use by the celioscopic route.

Once rehydrated, the film restores to the prosthetic fabric its initial mechanical properties (flexibility and elasticity) without fragmenting, and without making the fixation of the prosthesis more difficult. It is additionally transparent, and cannot stick when being put into position. Its rapid absorption ensures protection against the initial adhesive phenomena, that is to say in the first week following surgery, or in other words during the period of time necessary for the integration of the opposite surface. Upon its absorption, its weakly inflammatory and/or immunogenic character does not disturb the tissue colonization on the opposite side of said film.

The present invention will be better understood from the detailed description of a preferred embodiment, given by way of example, with reference being made to the appended figures, in which.

Figure 1:
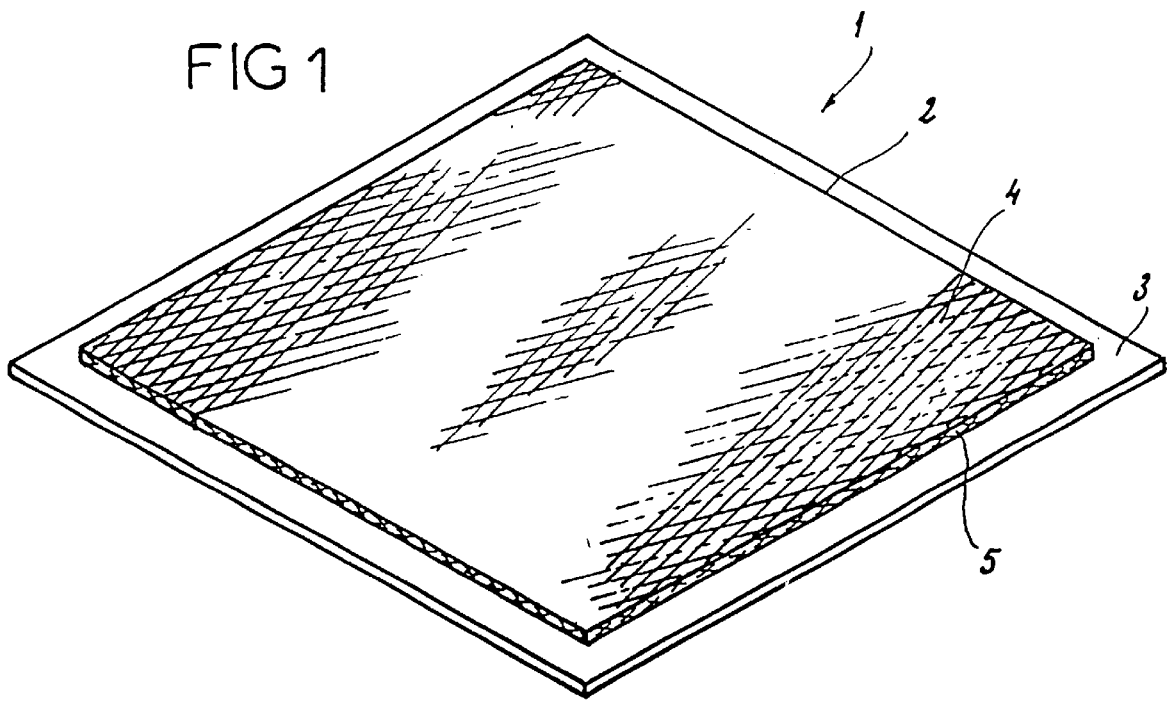
FIG. 1 is a perspective view of a composite prosthesis according to the invention.

Referring usefully to FIG. 1, a composite prosthesis according to the present invention is designated in a general manner by reference number 1. The prosthesis includes a prosthetic fabric 2 having two surfaces 4 and 5, one of which is covered with a film 3 of collagenous material. The prosthetic fabric 2 has an openwork three-dimensional structure, and in particular a "honeycomb" structure, and thus a certain thickness which separates the surface 4 from the surface 5. This fabric can preferably be obtained with a Rachel knit formed on a double needlebed. The spacing of the two needle beds and the delivery speeds of the yarns allow a finished fabric to be obtained in three dimensions (three-dimensional structure), with a thickness of between 1 and 3 mm, and for example of about 1.8 mm, for a weight of about 90 g/m$^2$. The final characteristics of the fabric are given independently of the knitting by the choice of basic material employed, for example multifilament 50 dtex PES polyester, the temperature, and the thermosetting time. Apart from the spinning, the yarn and the fabric do not receive any other treatment (no sizing or washing). Such a fabric without collagen has, in accordance with standard NFG 07119, a tensile strength of between about 18 daN and about 30 daN, and an elongation at break of about 25% to 37%, as warp, and a tensile strength of between about 9 daN and about 15 daN, and an elongation at break of about 60% to 88%, as weft.

Figure 7:
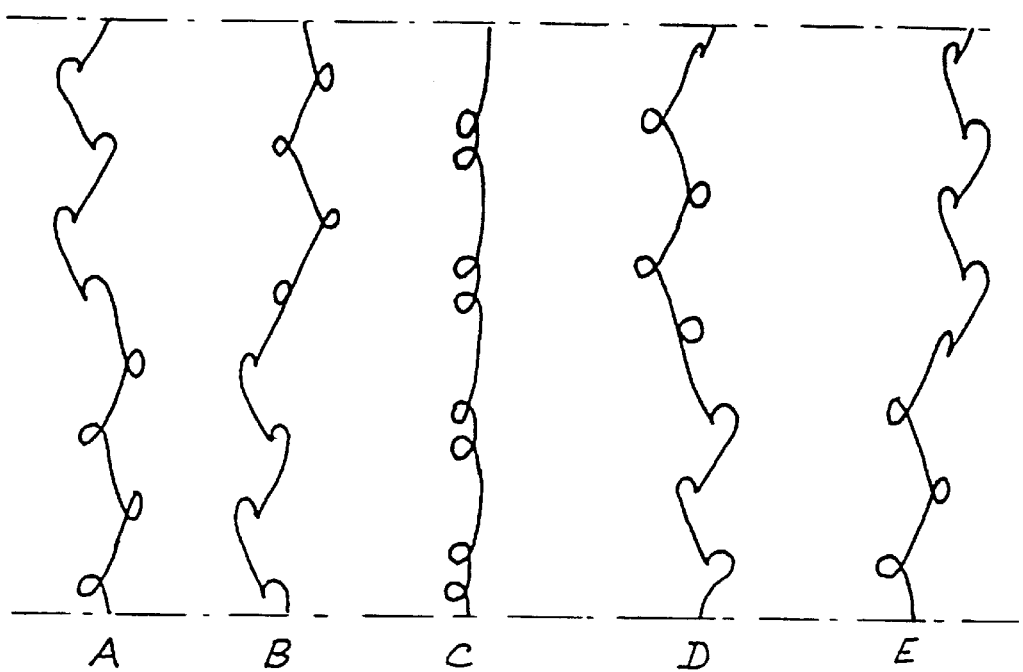
FIG. 7 represents a schematic drawing of the knitting weave of a prosthetic fabric forming part of a composite prosthesis according to the present invention.

Such a composite fabric can be formed by warp knitting of five layers of yarns, and in accordance with the diagrammatic sketch in FIG. 7. In this figure, each layer of yarns is identified by a letter, ranging from A to E, the sketch itself using a knitting description system which is entirely familiar and comprehensible to the person skilled in the art, and which will not be described in more detail here. According to FIG. 7, the preferred prosthetic fabric according to the present invention is, as has already been described, made up of two independent porous surfaces. In the given example, these two surfaces are themselves made up of two layers of yarns, labeled A, B and D, E respectively, the layers A, B giving a surface with tear-shaped openings, in order to accommodate and direct the postsurgical cell colonization, and the layers D, E giving a surface with hexagonal openings which will be closed by the film of collagenous material. The prosthetic fabric can be knitted on a double needlebed Rachel loom. In this case, all the bars corresponding to the yarns A, B and D, E are threaded one full/one empty. The layer of connecting yarns is represented by reference C and is threaded full. The different layers A–E of yarns are all knitted at the same time. Thus, the connecting yarns are distributed along the peripheral edges of the openings of each surface and extend substantially perpendicular from one surface to the other surface, preventing connecting yarns from occupying too great a volume of the transverse channels which are formed. The final fabric can then be stabilized simply by heating it in an oven to a temperature of between about 170° C. and about 220° C.

A composite prosthesis combining a prosthetic fabric of three-dimensional openwork structure, as described above, with a film of collagenous material can be produced in the following way.

The collagen-containing solution is modified beforehand by oxidative scission, heating, with a macromolecular hydrophilic additive, and optionally glycerol. Next, this solution is spread uniformly over a flat hydrophobic inert support in order to form a film resulting from two superposed thin layers.

To do this, a first thin layer of solution is applied, in which the weight concentrations of collagen, of macromolecular hydrophilic additive and of glycerol, if present, are preferably between, respectively, about 2 and 6% in the case of collagen, about 0.6 and 2% in the case of the macromolecular hydrophilic additive, and about 0.3 and 0.8% in the case of glycerol. This first thin layer has a density of between about 0.035 and about 0.27 g/cm$^3$, which represents about 70 to 90% of the final density of collagenous film present in the composite prosthesis. After this first thin layer has gelled by cooling, a second thin layer is applied to its surface, this being based on the same solution but preferably adjusted to an ethanol concentration of 5 to 50%. The second thin layer represents about 10 to 30% of the final density of collagenous film present in the composite prosthesis.

The prosthetic fabric of three-dimensional openwork structure, as obtained above, having a thickness of the order of 1.8 mm, is applied via its surface with hexagonal openings on the second thin layer, before gelling, so that anchoring takes place during the drying of the crosslinked collagen. After the reaction, the composite prosthesis is separated from the hydrophobic inert support.

Figure 2:
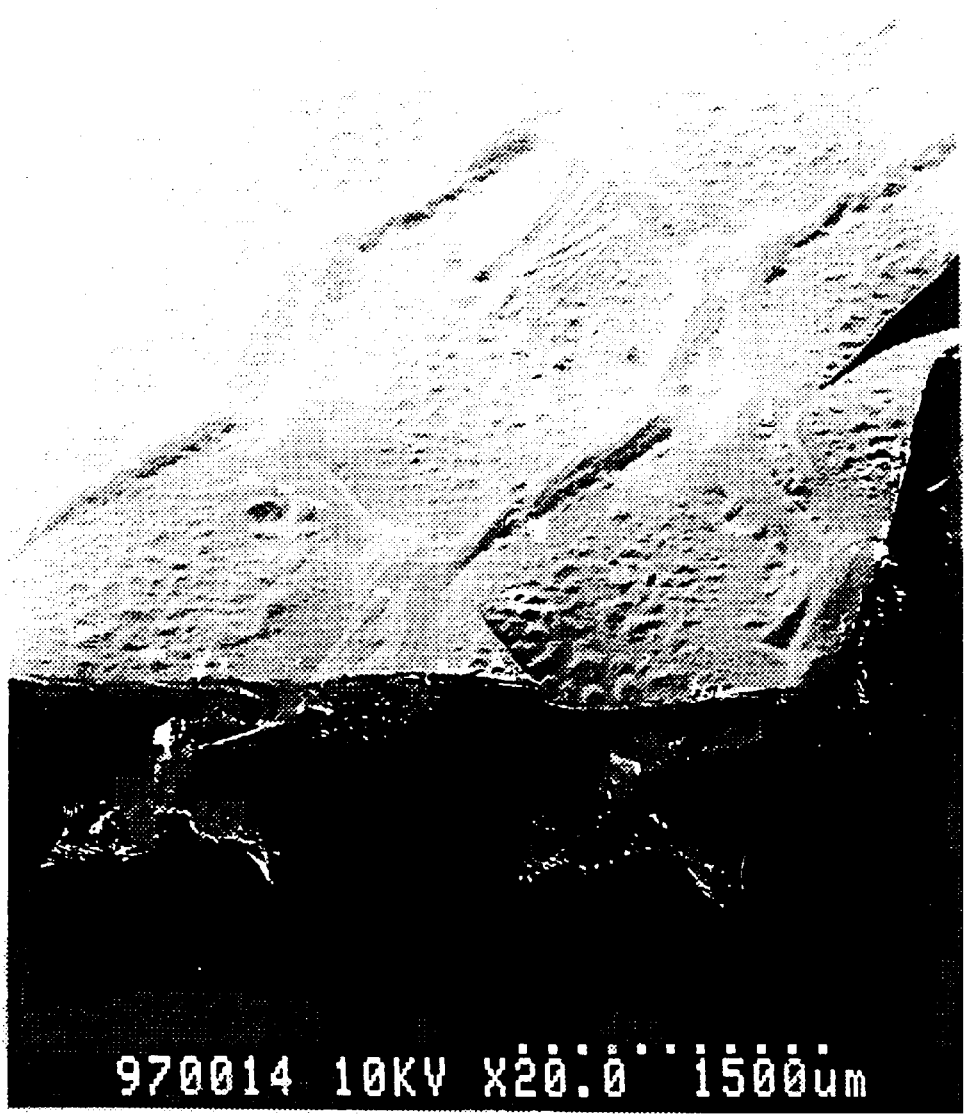
FIG. 2 is a microscope image of a prosthesis according to the invention, taken in perspective from the film side, on a magnified scale of 20 times the actual size.

FIG. 2 shows an image of a composite prosthesis obtained in the manner described, with a three-dimensional fabric.

Very clearly seen in FIG. 2 is the impression of the structure of the prosthetic fabric beneath the film of collagenous material, as well as the hexagonal shape of the transverse channels, and the twisting of the fibers making up the fabric. Also apparent at the bottom of the figure are parts of the prosthetic fabric, in cross section, which resemble upside-down "Y"s.

Figure 3:
FIG. 3 is a microscope image of the prosthesis of FIG. 2, on a magnified scale of 30 times the actual size.

FIG. 3 shows the same image, but on an even more magnified scale (30 times actual size). This image shows more clearly one of the parts in the form of an upside-down "Y" of the prosthetic fabric, as well as the edge of the film of collagenous material.

Figure 4:
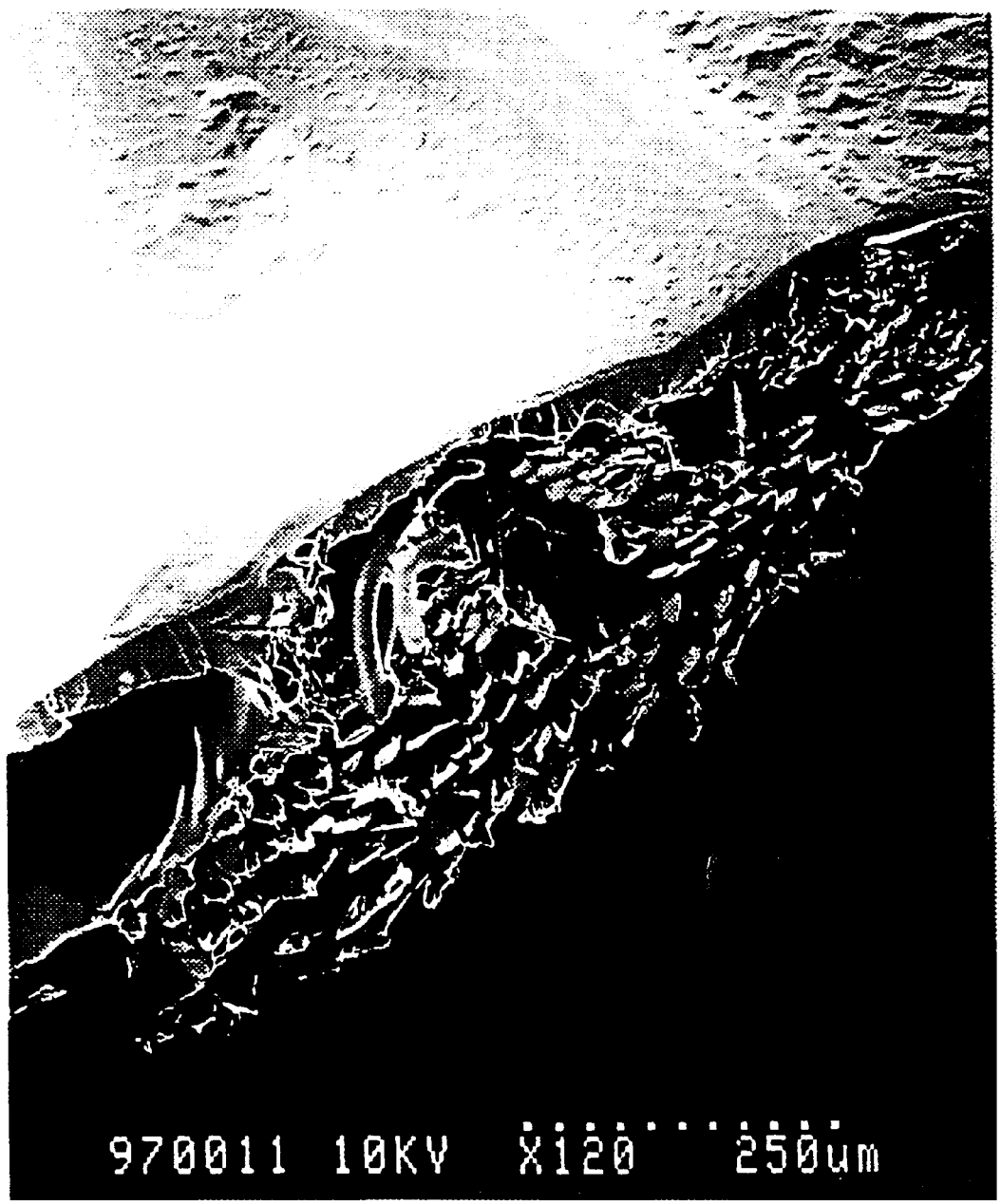
FIG. 4 is another microscope image of the same prosthesis of FIGS. 2 and 3, on a magnified scale of 120 times the actual size.

FIG. 4 shows the same prosthesis on a scale magnified to 120 times the actual size. This image clearly shows the edge of the film of collagenous material which, upon cutting for the requirements of photography, extends beyond the prosthetic fabric in the form of a skirt of material. In the lower left part, close to the left edge of the image, it will also be noted that the collagenous material has risen by capillary effect in the fibers, this effect being partly responsible for the high resistance to delamination of the film of the prosthetic fabric. Finally, in all FIGS. 2 to 4, it will be noted that the film is continuous and smooth, no synthetic fiber appearing on the surface.

Figure 5:
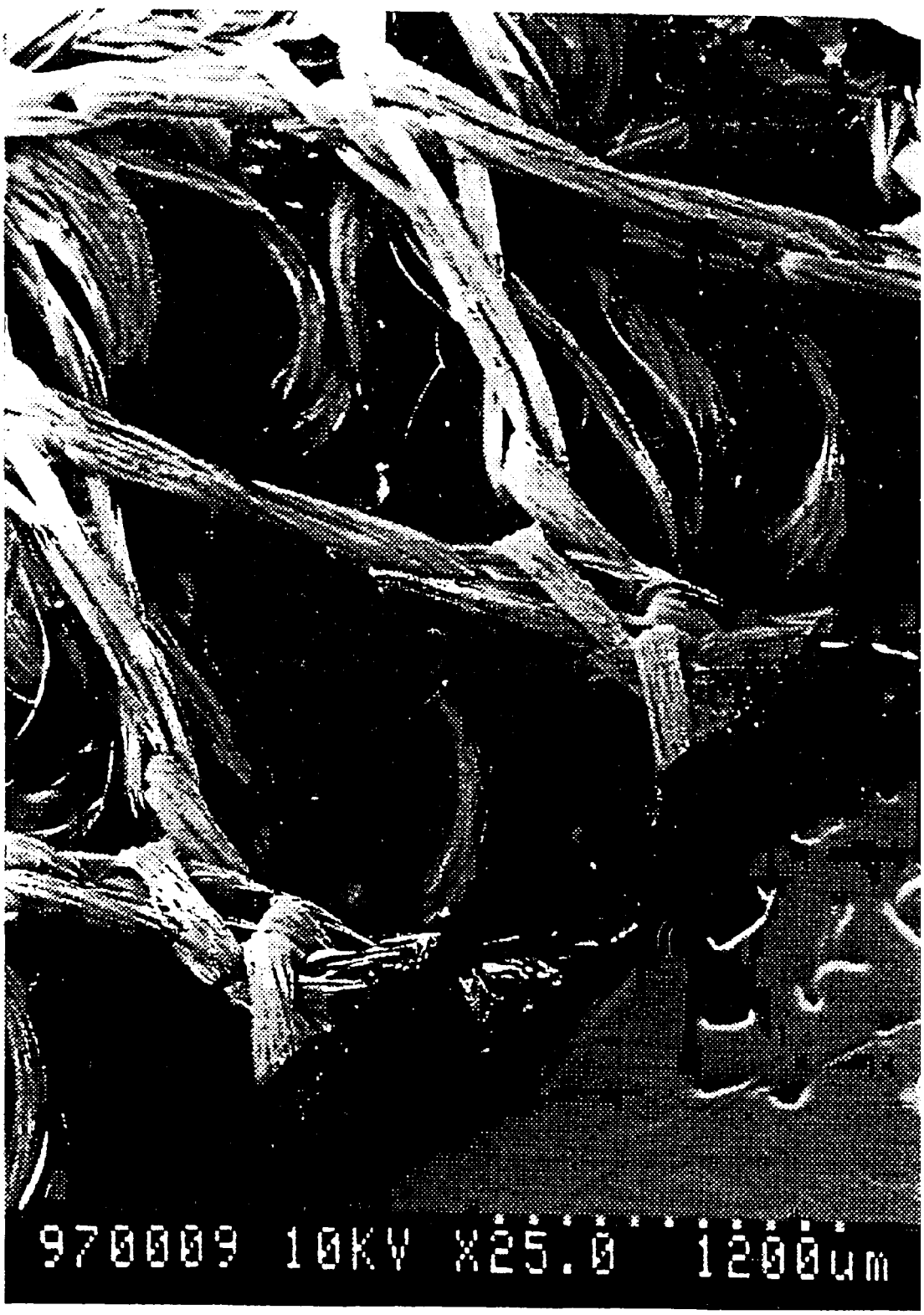
FIG. 5 is a microscope image of a composite prosthesis according to the invention, seen from the fabric side, on a magnified scale of 25 times the actual size.

FIG. 5 shows an image on the other side of the same prosthesis, that is to say on the fabric side, and clearly illustrates the three-dimensional openwork structure of the prosthetic fabric, with, on top [sic], the collagenous film which has a completely smooth internal surface.

Figure 6:
FIG. 6 is a cross-sectional microscope image of a composite prosthesis according to the invention, on a magnified scale of 40 times the actual size.

Finally, FIG. 6 shows a cross-sectional image, on a scale of 40 times the actual size, of the same prosthesis, in order to give an idea of the thickness of the film of collagenous material. This lies slightly to the right of an imaginary central line, the dark mass right at the right of the image being the photographic support. Thus, it is apparent that the film has a thickness of about 50 $\mu$m to 75 $\mu$m, but that the collagenous material has also been absorbed by capillary effect into the fibers of the prosthetic fabric to a depth of approximately 750 $\mu$m.

Clinical trials have been carried out on a model of cecal abrasion in rats, according to the protocol described by Harris et al. (1995) in "Analysis of the Kinetics of Peritoneal Adhesion Formation in the Rat and Evaluation of Potential Antiadhesive Agents", Surgery, 117(6), pages 663–669, which is widely used and validated for studies on postsurgical adhesions. The trials consist in creating an abrasion and dehydration over areas of 2 cm$^2$ of peritoneal wall and cecum wall, in contact with each other. The control group receives no product for protecting the wounds thus created. It is compared with groups of rats which receive a protective product, according to Table 1 below:

TABLE I

| | Incidence of surface-to-surface adhesions (number of animals/ total number of animals) | Area of adhesion (cm$^2$) | Percentage area of the adhesion with respect to the area of the lesion | Maximum force to break the adhesion formed (N) |
|---|---|---|---|---|
| Control | 44/45 | 1.27 | 63 | 1.25 |
| Interposition of a film of collagenous material | 0/10 | 0 | 0 | 0 |
| Interposition of a three-dimensional openwork prosthetic fabric | 12/12 | 1.62 | 81 | 1.28 |
| Interposition of a composite prosthesis according to the example of the invention | 1/12 | 0.11* | 6* | 0.37* |
| Interposition of a film based on hyaluronic acid (SEPRAFILM ®) | 2/10 | 0.85 | 43 | 0.93 |

*= values obtained for the one animal that developed a ceco-parietal adhesion.

The trials carried out with a composite prosthesis according to the invention show that it makes it possible to prevent adhesions right from the start of its implantation into the body and that the film in particular is absorbed in vivo in less than a week. Colonization of the prosthetic fabric takes place via the other surface, into the thickness of the three-dimensional structure, in such a way that the fabric is totally integrated into the body in order to completely fulfill its reinforcement function, especially in the treatment of eventrations, when the film is absorbed.

These results were confirmed after six postoperative weeks, a complete absence of adhesions having been noted.

What is claimed is:

1. Composite prosthesis, comprising:
   (a) a prosthetic fabric having a three-dimensional structure separating two surfaces of the fabric, at least one of said surfaces being open to any postsurgical cell colonization, and
   (b) at least one film of a cross-linked collagenous material that is linked, at least on a surface of the film, to the other said surface of said fabric, wherein said collagenous material comprises collagen having helical structure which is, at least partially, thermally denatured without hydrolytic degradation.

2. Prosthesis according to claim 1, characterized in that the prosthetic fabric has an openwork structure.

3. Prosthesis according to claim 1, characterized in that the collagenous material comprises at least one macromolecular hydrophilic additive chemically unreactive with respect to collagen.

4. Composite prosthesis according to claim 1, characterized in that the thickness of the film is less than the thickness of the prosthetic fabric.

5. Composite prosthesis according to claim 1, characterized in that the thickness of the film is between 2% and 10% of the total thickness of the composite prosthesis.

6. Composite prosthesis according to claim 1, characterized in that the thickness of the film is between approximately 30 $\mu$m and 100 $\mu$m.

7. Composite prosthesis according to claim 1, characterized in that the collagenous material comprises collagen modified by oxidative scission and heating above 37° C., crosslinked in the presence of at least one macromolecular hydrophilic additive chemically unreactive with respect to said collagen.

8. Composite prosthesis according to claim 7, characterized in that the collagen is modified by oxidative scission with the aid of periodic acid or one of its salts in order to make it self-crosslinkable.

9. Prosthesis according to claim 1, characterized in that the film is linked by capillary absorption to the constituent fibers of the prosthetic fabric.

10. Prosthesis according to claim 9, characterized in that the film is linked to the prosthetic fabric over a depth of less than 750 μm, measured from the outer surface of the film.

11. Prosthesis according to claim 3, characterized in that the macromolecular hydrophilic additive has a molecular weight of greater than 3000 daltons.

12. Prosthesis according to claim 11, characterized in that the macromolecular hydrophilic additive is a hydrophilic polymer having a molecular weight of between 3000 and 20,000 daltons.

13. Prosthesis according to claim 12, characterized in that the macromolecular hydrophilic additive is polyetylene glycol.

14. Prosthesis according to claim 3, characterized in that the collagenous material has a collagen/hydrophilic additive ratio of between 1:1 and 9:1.

15. Prosthesis according to claim 1, characterized in that the prosthetic fabric comprises two opposed porous surfaces, connected to each other by linking yarns, one of which is open to any postsurgical cell colonization and the other of which is closed to said colonization by the film of collagenous material.

16. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, said collagenous material comprising collagen and at least one macromolecular hydrophilic additive chemically unreactive with respect to collagen.

17. A composite prosthesis according to claim 16, wherein said collagen of said collagenous material has an helical structure which is, at least partially, thermally denatured without hydrolytic degradation.

18. A composite prosthesis according to claim 17, wherein said collagen of said collagenous material is obtained by modifying native collagen by an oxidative scission and heating above 37° C., and crosslinking said oxidated collagen in the presence of said hydrophilic additive.

19. A composite prosthesis according to claim 18, wherein said oxidative scission is made with the aid of periodic acid or one of its salts, in order to make said collagen self-crosslinkable.

20. A composite prosthesis according to claim 16, wherein said film is additional linked to said prosthetic fabric along said thickness by capillary absorption of said collagenous material before gelling to the constituent fibers of said prosthetic fabric.

21. A composite prosthesis according to claim 20, wherein said film is linked to said prosthetic fabric down to a depth of less than 750 μm, measured from the outer surface of said film.

22. A composite prosthesis according to claim 16, wherein said hydrophilic additive has a molecular weight greater than 3000 daltons.

23. A composite prosthesis according to claim 22, wherein said hydrophilic additive is a hydrophilic polymer having a molecular weight of between 3000 and 20,000 daltons.

24. A composite prosthesis according to claim 23, wherein said hydrophilic additive is polyethylene glycol.

25. A composite prosthesis according to claim 16, wherein said collagenous material has a collagen/hydrophilic additive ratio of between 1:1 to 9:1.

26. A composite prosthesis according to claim 25, wherein said collagenous material has a collagen/hydrophilic additive ratio of between 2:1 to 4:1.

27. A composite prosthesis according to claim 26, wherein said collagen/hydrophilic additive ratio is 3:1.

28. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, said collagenous material comprising collagen having an helical structure which is, at least partially, thermally denatured without hydrolytic degradation.

29. A composite prosthesis according to claim 28, wherein said collagen of said collagenous material is obtained by modifying native collagen by an oxidative scission and heating above 37° C., and crosslinking said oxidated collagen in the presence of said hydrophilic additive.

30. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface.

31. A composite prosthesis according to claim 30, wherein the weave of said prosthetic fabric determines, within said thickness, a multiplicity of said alveoli, which are substantially parallel to one another and open out on either of said first and second surfaces of said prosthetic fabric.

32. A composite prosthesis according to claim 31, wherein the internal section of said alveoli is substantially free of any linking yarn.

33. A composite prosthesis according to claim 32, wherein the thickness of said film is less than said thickness of said prosthetic fabric.

34. A composite prosthesis according to claim 33, wherein the thickness of said film represents between 2% and 10% of the overall thickness of said composite fabric.

35. A composite prosthesis according to claim 34, wherein the thickness of said film is between 30 μm and 100 μm.

36. A composite prosthesis according to claim 35, wherein the thickness of said film is between 50 μm and 75 μm.

37. A composite prosthesis comprising:
(a) a prosthetic non-absorbable fabric having a three-dimensional structure separating a first surface and a second surface opposite to said first surface, said first surface being open to any postsurgical cell colonization; and (b) at least one film of a crosslinked or gelled but absorbable collagenous material, linked to said prosthetic fabric over said second surface and along said thickness of said prosthetic fabric, by capillary absorption of said collagenous material, before gelling, to the constituent fibers of said prosthetic fabric.

38. A composite prosthesis according to claim 37, wherein said film is linked to said prosthetic fabric down to a depth of less than 750 μm, measured from the outer surface of said film.

39. A composite prosthesis comprising:
(a) a prosthetic non-absorbable fabric having a three-dimensional structure having a thickness separating a first surface and a second surface opposite to said first surface, said first surface presenting alveoli open to any postsurgical colonization, said alveoli passing completely through said prosthetic fabric; and
(b) at least one film of a crosslinked or gelled but absorbable collagenous material, linked to said prosthetic fabric at least over said second surface, said collagenous material comprising collagen and at least one macromolecular hydrophilic additive chemically unreactive with respect to collagen.

40. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, the surface of said film opposite to said prosthetic fabric being substantially smooth and non porous.

41. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, said film projecting beyond the edges of said prosthetic fabric.

42. A composite prosthesis according to claim 41, wherein the overshoot between said film and said prosthetic fabric is from 5 to 10 millimeters.

43. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, said film being in dehydrated form, and arranged to substantially restore in rehydrated form the initial mechanical properties of said prosthetic fabric.

44. A composite prosthesis comprising:
(a) a prosthetic non-absorbable fabric the weave of which determines a three-dimensional structure having a thickness separating a first surface and a second surface opposite to said first surface, said first surface having alveoli open to any postsurgical cell colonization; and
(b) at least one film of a crosslinked collagenous material, linked to said prosthetic fabric at least over said second surface.

45. A composite prosthesis according to claim 44, wherein said prosthetic fabric is obtained with a Rachel knit formed on a double needlebed.

46. A composite prosthesis according to claim 45, wherein said knit is obtained by warp knitting five layers of yarns, in accordance with the diagrammatic sketch in FIG. 7.

47. A composite prosthesis according to claim 45, wherein said prosthetic fabric is formed by warp knitting, and comprises two independent porous surfaces and a layer of connecting yarns extending substantially perpendicular to said first and second surfaces.

48. A composite prosthesis according to claim 47, wherein each independent porous surface of said prosthetic fabric is made up of two layers of yarns.

49. A composite prosthesis according to claim 48, wherein one independent porous surface of said prosthetic fabric forms said first surface and has tear-shaped openings, and the other independent porous surface forms said second surface and has hexagonal openings.

50. A composite prosthesis comprising:
(a) a prosthetic non-absorbable fabric having a three-dimensional structure having a thickness separating a first surface and a second surface opposite to said first surface, said first surface having alveoli open to any postsurgical cell colonization; and
(b) at least one film of a crosslinked or gelled but absorbable collagenous material, linked to said prosthetic fabric at least over said second surface, said film comprising two superposed thin layers of a collagenous material.

51. A composite prosthesis according to claim 50, wherein the first thin layer represents about 70 to 90% of the final density of said collagenous film.

52. A composite prosthesis according to claim 50, wherein the second layer represents about 10 to 30% of the final density of said collagenous film.

* * * * *